US009375657B2

(12) United States Patent
Oroskar et al.

(10) Patent No.: US 9,375,657 B2
(45) Date of Patent: Jun. 28, 2016

(54) FLASH CHROMATOGRAPHY COLUMN APPARATUS

(71) Applicant: Orochem Technologies, Inc., Naperville, IL (US)

(72) Inventors: Anil R. Oroskar, Oak Brook, IL (US); Asha A. Oroskar, Oak Brook, IL (US); Ved Bhushan Gulati, Downers Grove, IL (US); Rakesh Vikraman Nair Rema, Downers Grove, IL (US)

(73) Assignee: Orochem Technologies, Inc., Naperville, IL (US)

( * ) Notice: Subject to any disclaimer, the term of this patent is extended or adjusted under 35 U.S.C. 154(b) by 336 days.

(21) Appl. No.: 14/077,286

(22) Filed: Nov. 12, 2013

(65) Prior Publication Data

US 2015/0129501 A1 May 14, 2015

(51) Int. Cl.
*G01N 30/60* (2006.01)
*B01D 15/16* (2006.01)
*G01N 30/56* (2006.01)

(52) U.S. Cl.
CPC .............. *B01D 15/165* (2013.01); *G01N 30/60* (2013.01); *G01N 30/6004* (2013.01); *G01N 30/6026* (2013.01); *G01N 2030/562* (2013.01); *G01N 2030/565* (2013.01)

(58) Field of Classification Search
None
See application file for complete search history.

(56) References Cited

U.S. PATENT DOCUMENTS

| 4,293,422 | A | 10/1981 | Still |
| 4,591,442 | A | 5/1986 | Andrews |
| 5,264,119 | A | 11/1993 | Rollins |
| 6,171,486 | B1 | 1/2001 | Green |
| 7,166,215 | B2 | 1/2007 | Reid |
| 7,361,214 | B2 | 4/2008 | Arno |
| 7,381,327 | B2 | 6/2008 | Ellis |
| 2003/0102266 | A1 | 6/2003 | Ritacco |
| 2004/0154969 | A1* | 8/2004 | Thompson ......... G01N 30/6004 210/198.2 |
| 2005/0011835 | A1* | 1/2005 | Henderson ............ B01D 15/22 210/656 |
| 2005/0287062 | A1 | 12/2005 | Aznar |
| 2010/0206813 | A1* | 8/2010 | Yukon ................... B01D 15/22 210/656 |
| 2011/0180481 | A1* | 7/2011 | Chordia ................. B01D 15/20 210/656 |
| 2013/0341482 | A1* | 12/2013 | Uselius ................. B01D 15/08 248/514 |

OTHER PUBLICATIONS

Reference: Mesh Micron Conversion Chart. ICPI Workshop 2011.*

* cited by examiner

*Primary Examiner* — Katherine Zalasky
*Assistant Examiner* — Kara Graber
(74) *Attorney, Agent, or Firm* — Richard P. Silverman & Assoc., LLC

(57) ABSTRACT

A flash chromatography apparatus which provides an improved apparatus for large and medium commercial scale flash chromatography columns. More particularly, the invention relates to a flash chromatography column and cartridge system for positioning and ease of loading and unloading of stationary phase agent in the flash chromatography column. The flash chromatography column further provides flow distributors to support the stationary phase and permit plug flow through the column. The apparatus of the present invention is a modular and can be disposed in any configuration to reduce maintenance cost and downtime in a commercial installation. Flash chromatography is widely used for purification of low molecular weight organic compounds and products of organic synthetic reactions.

18 Claims, 9 Drawing Sheets

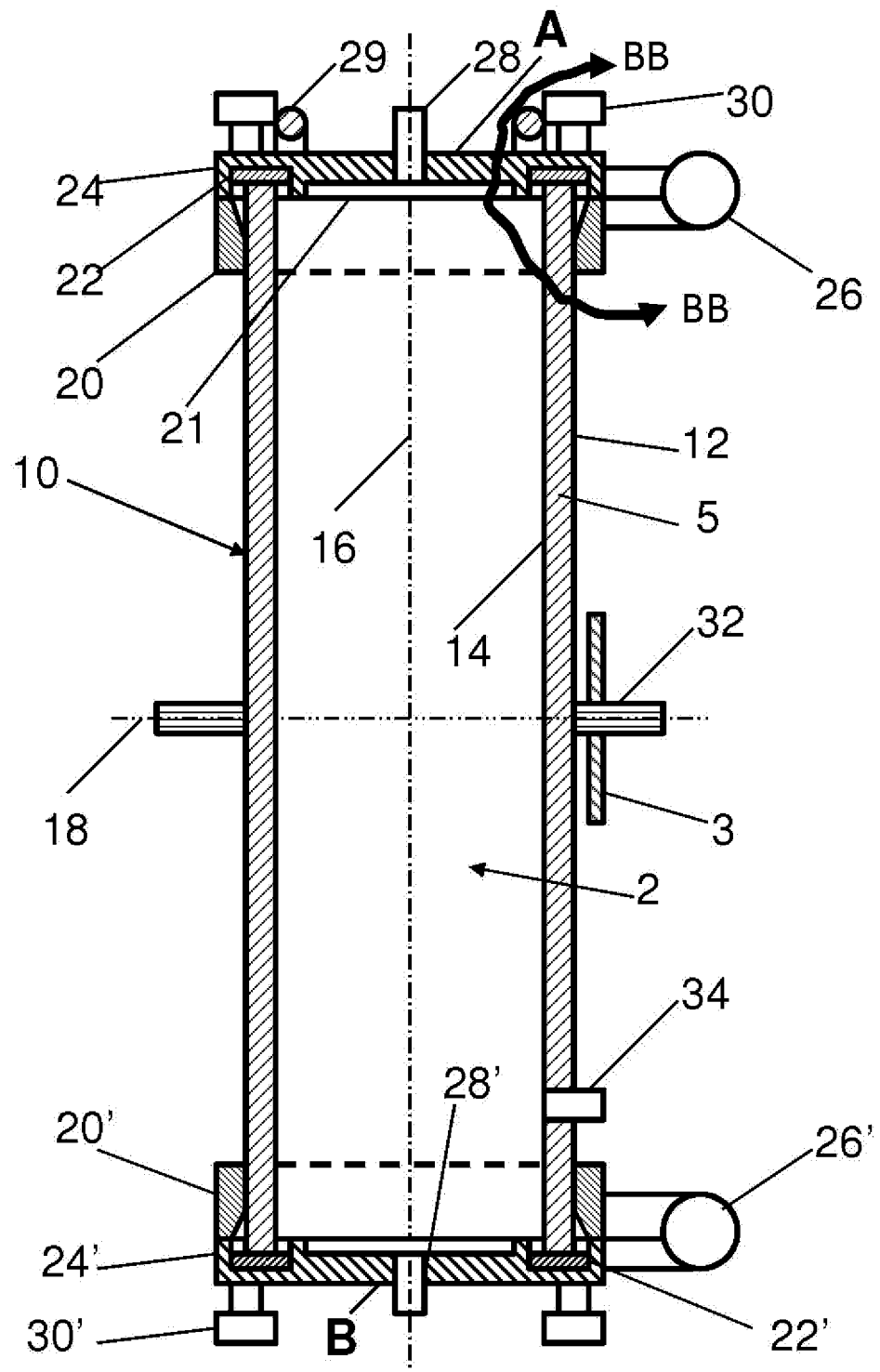

FLASH CHROMATOGRAPHY COLUMN APPARATUS

FIELD OF THE INVENTION

This invention is generally concerned with an improved apparatus for use in large and medium commercial scale flash chromatography columns. More particularly, the invention relates to a flash chromatography column and cartridge system for positioning and ease of loading and unloading of stationary phase agent in the flash chromatography column. The flash chromatography column further provides flow distributors to support the stationary phase and permit plug flow. The apparatus of the present invention is modular and can be disposed in any configuration to reduce maintenance cost and downtime in a commercial installation.

BACKGROUND

Chromatography is a technique used to, among other things, separate component elements of a starting material. Within the general field of chromatography, there are several types. Supercritical fluid chromatography (SFC) is a high pressure, reverse-phase method that typically operates above the critical point of the mobile phase fluid, and offers significant speed advantage and resolution over traditional techniques such as high performance liquid chromatography (HPLC). SFC employs carbon dioxide or another compressible fluid as a mobile phase, sometimes with a co-solvent, to perform a chromatographic separation. SFC has a wide range of applicability and typically uses small particle sizes of 3-20 microns for column packing material and is for analytical to preparative scale applications because of the lower pressure drop. In HPLC applications pressure at the top of the column typically reaches up to 1000 psi but pressure at the bottom is reduced to ambient pressure, creating a significant pressure drop.

Liquid chromatography (LC) applies to a cruder, lower pressure, lower performance technique for simple separations. Flash chromatography is a form of adsorptive chromatography and is subset of LC that uses a very simple, porous stationary phase with particle sizes nearer to 100 microns often in a disposable cartridge, or column. Because the particles in the packing material are larger and often irregular, the columns are much cheaper and are considered disposable. Pressure at the top of the column in flash chromatography applications is typically up to 100 psi and dropping down to ambient at the bottom of the column. Still (U.S. Pat. No. 4,293,422) describes a method of adsorptive chromatography in which the mobile phase is first admitted into a space above an adsorbent bed of silica gel, then pushed through the bed with gas pressure. Once the space is cleared, the mobile phase with dissolved compounds for analysis is admitted, and it too is pushed into the bed, displacing the earlier charge of neat mobile phase. Then in a third step, a second charge of neat mobile phase forces the solution through the bed, causing fractionation of the solute. A subsequent disclosure by Andrews (U.S. Pat. No. 4,591,442) describes a similar device, the main difference being in the placement of the liquid holding space. Both disclosures focus on mechanical design and methods for achieving flash chromatography at relatively low pressure. More recently, Ritacco (US App. 2003/0102266) describes a convenient polymer-encased cartridge for use as a single ended flash chromatography column. Anzar (WO/2004-051257, US App. 2005/0287062) describes another type of pre-filled cartridge for flash chromatography. Common features of all of these disclosures are (1) an emphasis on instrumental convenience, and (2) the use of an adsorptive bed that allows for fast, although imprecise, separation of solutes. The disclosures also emphasize gas and liquid chromatography applications of low to moderate pressure.

The majority of all separations in flash chromatography use a normal phase technique with solvents such as methanol, ethanol, hexane, and heptane and occasionally the reverse phase technique with water and acetonitrile. Chemists buy thousands of flash chromatography systems per year to use primarily as a simple, repeatable normal phase purification technique. Because of the vast number of flash chromatography systems in medicinal chemistry laboratories in pharmaceutical research environments, users, insurers, regulators and environmentalists are growing increasingly concerned with the vast amount of toxic waste solvent generated at these sites. Given the obvious problems associated with unsafe, toxic, flammable solvents, a new simple, normal phase technique must be found that is fast and uses less toxic solvents.

SUMMARY OF THE INVENTION

The present invention provides an opportunity to carry out flash chromatography in a flash chromatography process with medium to large size samples. The apparatus of the present invention can support an adsorbent capacity of from about 10 to about 50 kilograms of adsorbent (more preferably, the adsorbent capacity ranges from about 25 to about 50 kilograms) in a chamber which can be pressurized to operate over an operating pressure range of from about 100 psia (pounds per square inch absolute) (7.82 atm) to about 150 psia (11.23 atm). The amount of the adsorbent in the apparatus can be disposed within the apparatus by means of inert spacers. The modular design permits either a single apparatus or an apparatus having multiple chambers to be arranged for convenient maintenance operation.

In one embodiment, the invention is a modular apparatus for performing flash chromatography. The apparatus comprises a chamber comprising a cylindrical shell, a proximal and a distal annular ring, a proximal and a distal cover plate, a flash chromatographic cartridge, a gasket, a pair of pivot shafts, and a stationary horizontal base. The cylindrical shell has a proximal end and a distal end. The cylindrical shell encloses a hollow cylindrical interior, and has outer surface and an interior surface, a centerline and a midpoint along the centerline. The proximal annular ring and a distal annular ring are each sealingly disposed at the proximal end and at the distal end of the cylindrical shell, respectively. Each annular ring has an upper surface, a hinge and a plurality of mounting clamps distributed uniformly about each annular ring. The upper surface has a raised ring. Both the proximal cover plate and a distal cover plate, each have a center, an outer side, an underside, and a nozzle. The underside of each cover plate has disposed thereon a registration channel, a sealing channel concentric with the registration channel, and a plurality of radial flow distribution channels extending radially from a distribution hub at the center and extending toward the registration channel.

Each raised ring on the proximal and distal annular rings is adapted to be disposed in the registration channel when each cover plate is in a closed position. Each cover plate is removably disposed on the annular ring at the distal end and at the proximal end of the cylindrical shell and rigidly attached to said hinge to properly register the cover plate on the annular ring and to permit the cover plate to be sealingly disposed on the annular ring and secured by the plurality of mounting clamps. Each nozzle is in fluid communication with the hollow cylindrical interior. A flash chromatographic cartridge is disposed in the hollow cylindrical interior. The flash chromatographic cartridge having a proximal end and a distal end comprises a cylindrical cartridge shell, a first and second porous frit plate and a porous support plate. The cylindrical cartridge shell encloses a hollow cartridge interior. The first porous frit plate is sealingly disposed toward the proximal end and a second porous frit plate is sealingly disposed toward the distal end of the cylindrical cartridge shell. Each porous support plate is disposed over the respective frit plate and rigidly attached to the cylindrical cartridge shell toward the proximal and distal ends such that at least a portion of the cylindrical shell extends beyond the porous support plate to provide a raised proximal ring and a raised distal ring adapted to be positioned within the sealing channel of each cover plate adjacent to the cylindrical shell when each cover plate is in the closed position. A stationary phase adsorbent is disposed in the hollow cartridge interior such that the stationary phase adsorbent is in fluid communication with the hollow cylindrical interior. The gasket is disposed in the sealing channel of each cover plate to provide a seal between each annual ring and each cover plate and between the cylindrical cartridge shell and each cover plate. A pair of pivot shafts is rigidly disposed on the outer surface of the cylindrical shell at the midpoint and extending outwardly from the outer surface along a line at right angles to the centerline. A stationary horizontal base has a pair of upright members. Each of the upright members extends above the stationary horizontal base at a 90 degree angle relative to the stationary horizontal base and terminates in a bearing which is adapted to receive the pair of pivot shafts. The cylindrical shell can be positioned vertically or horizontally relative to the stationary horizontal base.

BRIEF DESCRIPTION OF THE DRAWINGS

FIG. 2a is a cross-sectional view of the chamber of one embodiment of the invention.

DETAILED DESCRIPTION OF THE INVENTION

Flash chromatography is useful for rapid, preparative separations with moderate resolution. Flash chromatography is widely used for purification of low molecular weight organic compounds and products of organic synthetic reactions. Such organic compounds can include proteins, oligosaccharides, DNA molecules and virus particles. Modern flash techniques include the use of convenient disposable flash cartridges instead of glass columns. Flash purification systems allow users to speed up the purification process for quicker results and higher throughput. Flash chromatography does not provide the resolution or reproducibility of HPLC; it is a technique that is employed to improve the purity of samples to an acceptable level or prepare samples for further purification.

As used herein in the specification and claims, including as used in the examples and unless otherwise expressly specified, all numbers may be read as if prefaced by the word "about", even if the term does not expressly appear. Also, any numerical range recited herein is intended to include all subranges subsumed therein.

Figure 1:
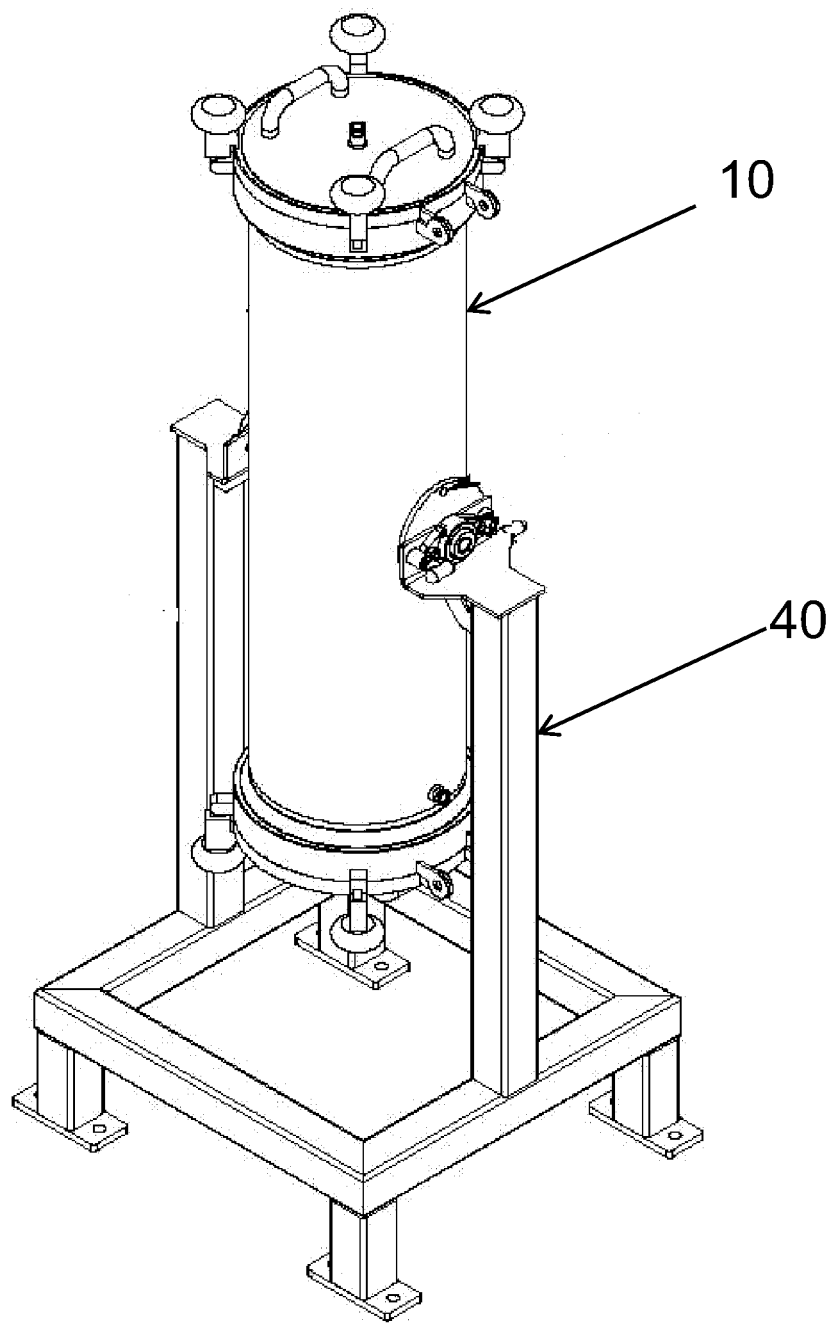
FIG. 1 is a schematic representation of a preferred embodiment of the modular apparatus of the present invention showing a chamber and a modular base.

Referring to FIG. 1, a modular flash chromatographic apparatus is shown for performing flash chromatography separation. The modular flash chromatographic apparatus includes a chamber 10 and a modular base 40.

Figure 2B:
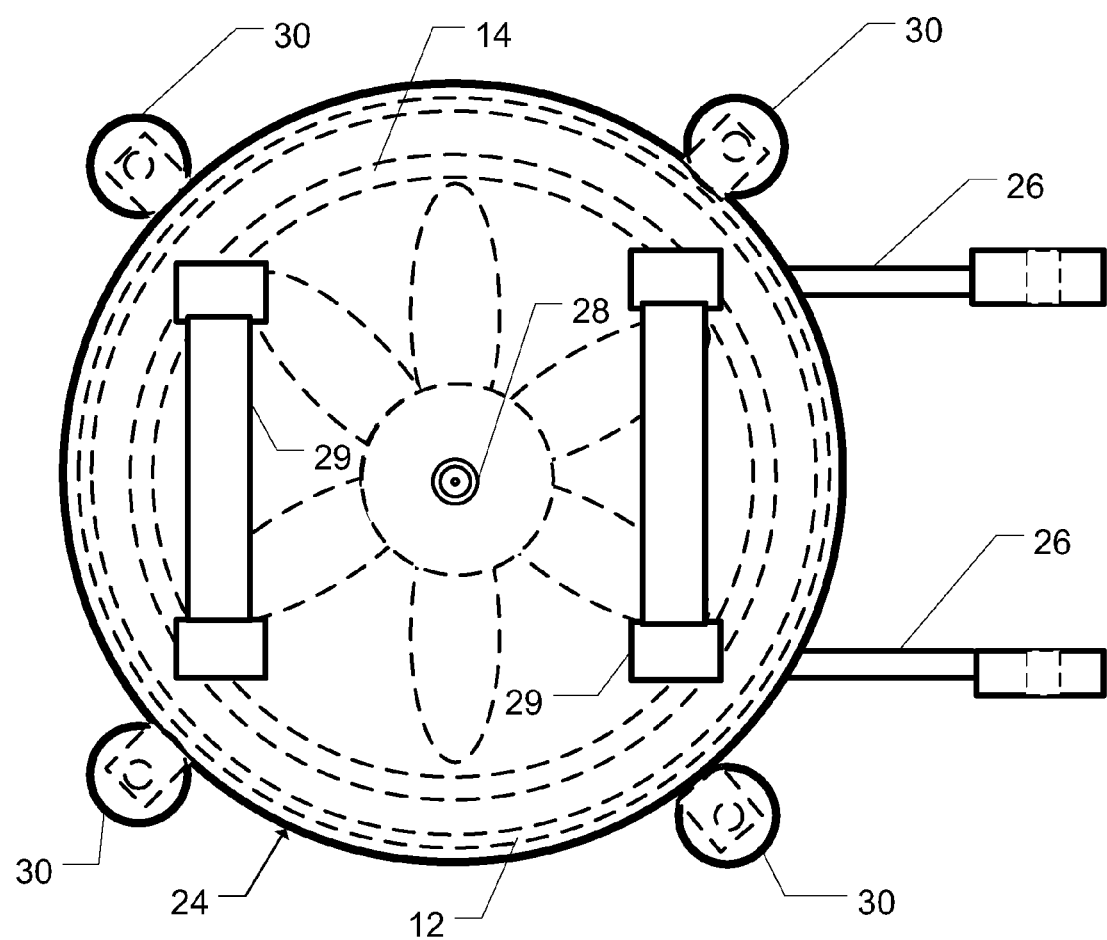
FIG. 2b is a top view of the chamber of one embodiment of the invention.

Referring to FIGS. 2a, 2b, 2c, 2d and 2e, the chamber 10 includes a cylindrical shell 5 having a proximal end A and a distal end B. The cylindrical shell 5 encloses a hollow cylindrical interior 2 and has an outer surface 12 and an interior surface 14. The cylindrical shell 5 has a centerline 16 and a midpoint 18 along the centerline. A proximal annular ring 20 is sealingly disposed at the proximal end A and a distal annular ring 20' is sealingly disposed at the distal end B of the cylindrical shell 5. Each annular ring has a hinge 26 (or 26') and a plurality of mounting clamps 30 (or 30') distributed uniformly about the annular ring (20 or 20'). There are two identical circular cover plates (24, 24') removably disposed at the proximal and the distal ends of the cylindrical shell 5. A first cover plate 24 which has an input nozzle 28 in the center, is removably disposed on the proximal annular ring 20, and a second cover plate 22' which has an outlet nozzle 28' is removably disposed on the distal annular ring 24'. A weep nozzle 34 is disposed near the distal end of the cylindrical shell in fluid communication with the hollow cylindrical interior 2 to provide for the draining of any fluid from the chamber prior to servicing the chamber or removing a stationary phase adsorbent cartridge (See FIG. 5). The weep nozzle 34 on the hollow cylinder can be used for providing radial nitrogen pressure to the stationary adsorbent cartridge which results in better sealing of the stationary adsorbent cartridge in the chamber 10. The first and second cover plates 24 are mirror images of each other and include a nozzle 28 in the center of each cover plate, and a concentric registration channel 36, a concentric sealing channel 35, and a plurality of radial flow distribution channels 8 extending radially from a distribution hub 21 toward the registration channel disposed on an underside of each cover plate 24 (See FIG. 2e for details of the cover plate). A gasket or o-ring 22 is disposed in the sealing channel 35. The sealing channel 35 is adapted to accommodate an end portion of the cylindrical shell 5 and a portion of the cylindrical outer wall 120 of the stationary adsorbent cartridge 100 (See FIG. 5) when in the closed or sealed position, wherein the end portion of the cylindrical shell and the cylindrical outer wall 120 of the stationary adsorbent cartridge 100 are in contact with the gasket 22 in the sealing channel 35. The first cover plate 24 is rigidly attached to the hinge 26 to properly register and seat the first cover plate 24 on the proximal annular ring 20 and to permit the first cover plate 24 to be sealingly disposed on the proximal annular ring 20 and secured by the plurality of mounting clamps 30. The annular ring includes a raised ring 38 adapted to be disposed in the registration channel 36 when the cover plate 24 is in the closed or sealed position relative to the annular ring 20. Similarly, the second cover plate 24' is rigidly attached to the hinge 26' to properly register and seat the second cover plate 24' on the distal annular ring 20' and to permit the second cover plate 24' to be sealingly disposed on the distal annular ring 20' when in the closed or sealed position. Each cover plate is secured to each annular ring by a plurality of mounting clamps 30 and 30'. Each clamp has a clamp assembly for connecting and disconnecting the registered cover plates to the annular rings. Typically, the clamp assembly has a pair of clamp segments (30 upper and 31 lower as shown in FIG. 2*b*) and at least one cam, spring or threaded shaft (not shown) in operable engagement with the clamp segments. The clamp segments are movable between a closed position to engage the cover plates and an open position to disengage from the cover plates. At least one or a pair of handles 29 are optionally disposed on the outer side of the cover plates to facilitate the movement of the chamber between a vertical and a horizontal position and to provide stability in opening or closing the cover plate. The gaskets 22 and 22' are in the form of o-rings which can be composed of VITON® resin, a fluoroelastomer resin (available from E.I. du Pont de Nemours and Company, Wilmington, Del.), TEFLON®, a polytetrafluoroethylene PTFE (available from E.I. du Pont de Nemours and Company, Wilmington, Del.), chlorinated polyethylene (CPE), and asbestos. A gasket comprising a silicon encapsulate with PTFE is preferred. The inlet nozzle and the outlet nozzles are in fluid communication with the hollow cylindrical interior 2. A pair of pivot shafts 38 are rigidly disposed on the outer surface 12 of the cylindrical shell 5 at the midpoint 18. A pivot positioning wheel 3 is disposed on at least one of the pivot shafts for the manual movement of the chamber from a vertical position to a horizontal position. The pivot shafts 38 extend outwardly from the outer surface 12 along a line at a right angle to the centerline 16. The chamber 10 is supported by a modular base 40 in a manner which permits the chamber 10 to be rotated between a vertical position and a horizontal position. The orientation of the hinge (26 and 26') is in line with the pivot shafts to permit the cover plate (24 or 24') to be opened on a horizontal plane relative to the stationary horizontal base. Preferably, the chamber comprises materials selected from the group consisting of stainless steel, corrosion resistant alloy, metals having a fluoropolymer coating, and mixtures thereof. More preferably, the chamber comprises stainless steel or corrosion resistant steel.

Figure 2C:
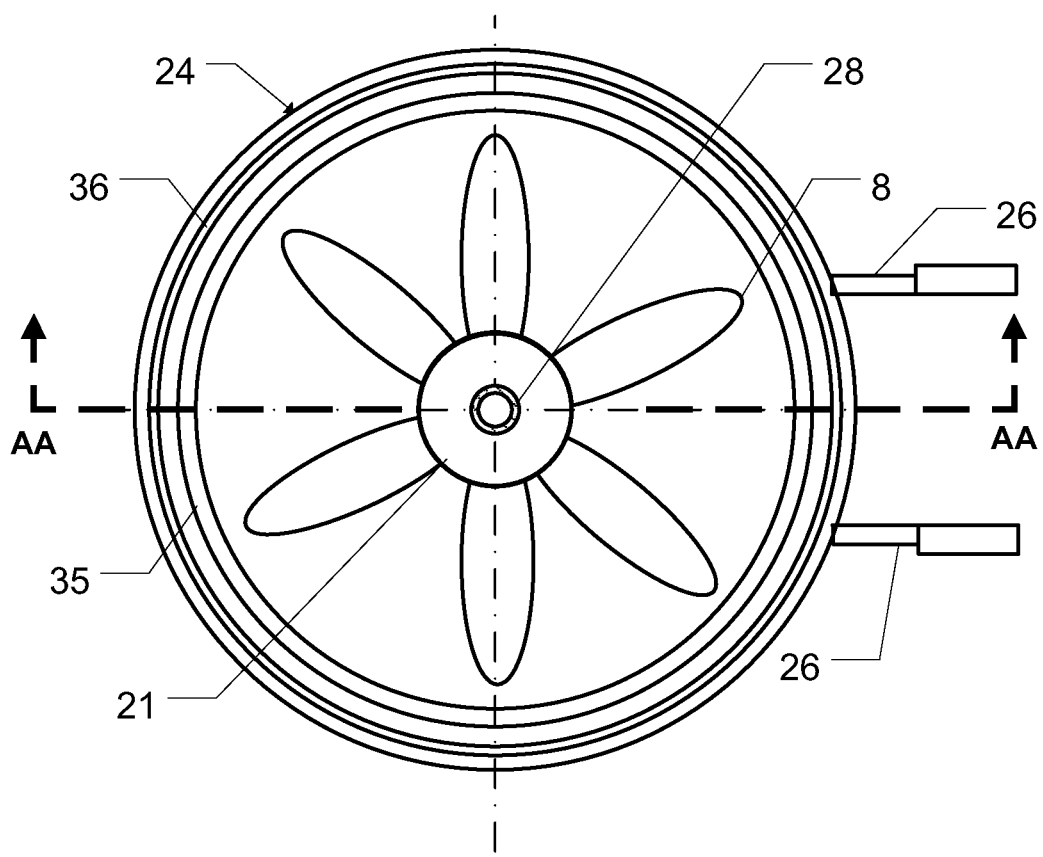
FIG. 2c is a bottom view of the cover plate of one embodiment of the invention.

With reference to FIG. 2*c*, an underside view of a cover plate 24 or 24' is shown. The following description applies to the cover plate at both the distal and the proximal ends of the cylinder 10. The cover plate 24 includes a registration channel 36 adapted to receive the registration ring 38 on the annular ring 20, a sealing channel 35 adapted to receive the proximal or distal end of the cylindrical shell 5 and a portion cylindrical outer wall 120 of the stationary adsorbent cartridge. The underside of each cover plate 24 includes a plurality of radial flow distribution channels 8 extending radially from a distribution hub 21. The hinge 26 is shown rigidly disposed on the cover plate.

Figure 2D:
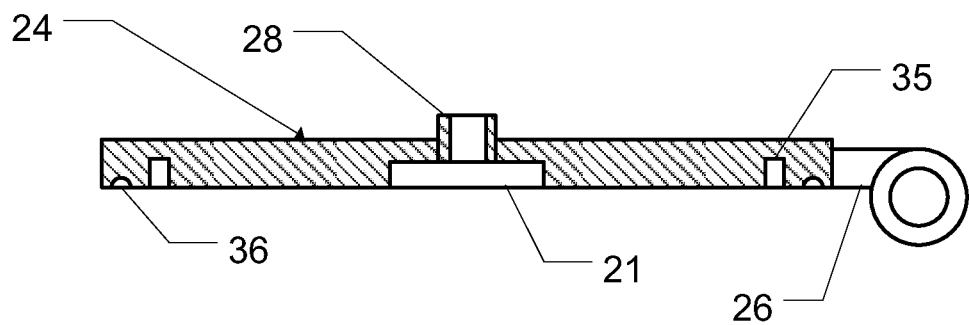
FIG. 2d is a cross-sectional view of the cover plate of one embodiment of the invention.

With reference to FIG. 2*d*, a cross-sectional view of the cover plate at section AA in FIG. 2*c* is shown. The nozzle 28 is shown extending through the cover plate 24 in fluid communication with the distribution hub 21. The registration channel 36 and the sealing channel are shown in relation to the hinge 26 and the nozzle 28.

Figure 2E:
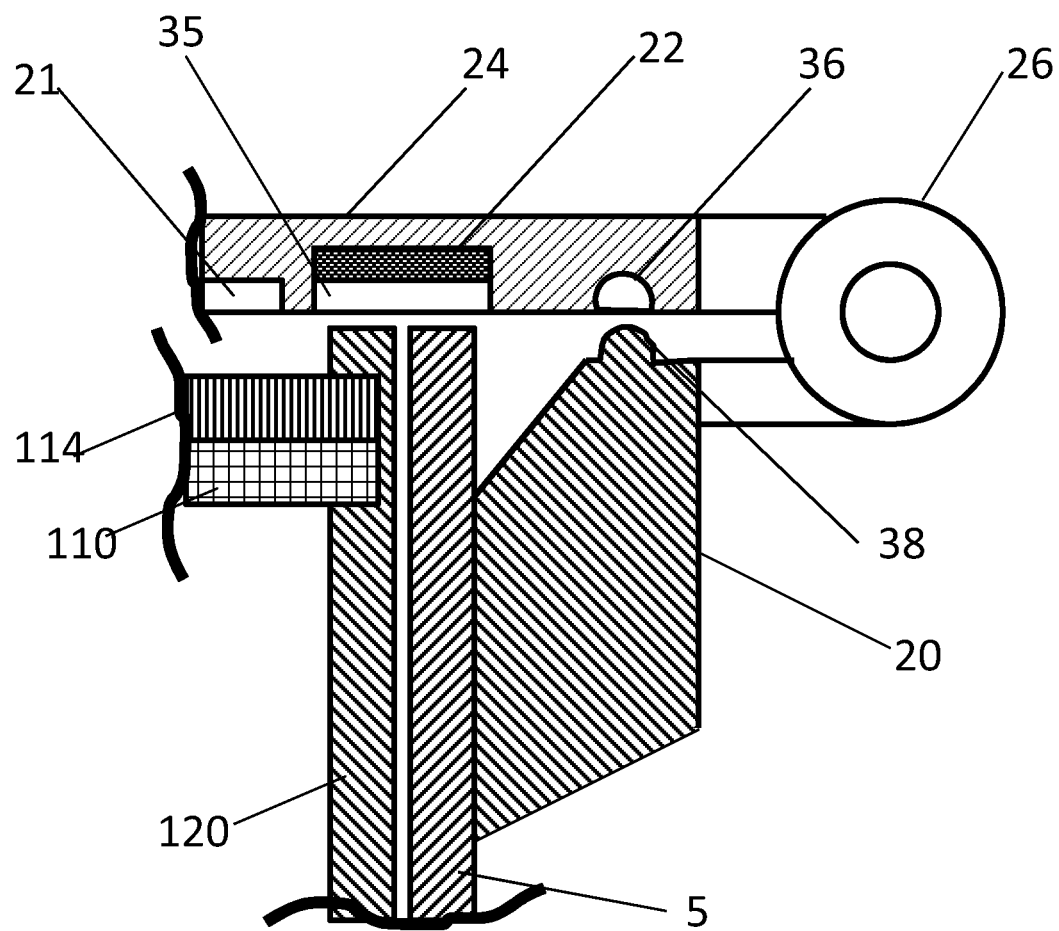
FIG. 2e is a detail view of a corner of the chamber at Section BB of one embodiment of the invention.

With reference to FIG. 2*e* which is a schematic drawing showing the detail of the proximal and distal ends of the cylindrical shell 5 at Section BB of FIG. 2*a* and provides details on the annular ring and cover plate to show how the seal and registration of the cover plate and annular ring achieve a seal and engage both the cylindrical shell and the cylindrical outer wall 120 of the stationary adsorbent cartridge within the sealing channel 35. Proper registration of the cover plate is maintained by hinge 26 and the a raised ring 38 adapted to be disposed in the registration channel 36 when the cover plate 24 is in the closed or sealed position. When the stationary adsorbent cartridge is inside the cylindrical shell 5, the cylindrical outer wall is adjacent to the interior surface 14 of the cylindrical shell 5. The portion of the cylindrical outer wall 120 of the stationary adsorbent cartridge extending beyond the porous support plate 114 and the frit plate 110 extends into the sealing channel 35. The distribution hub 21 disposed on the underside of each cover plate 24 is shown for reference purposes.

Figure 3A:
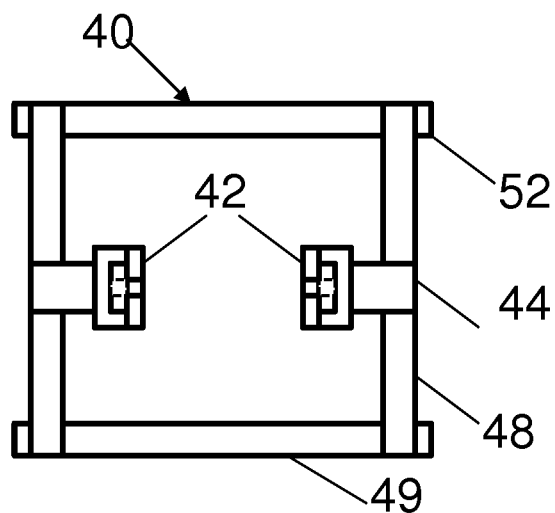
FIG. 3a is a top view of one embodiment of the modular base of the invention.
Figure 3B:
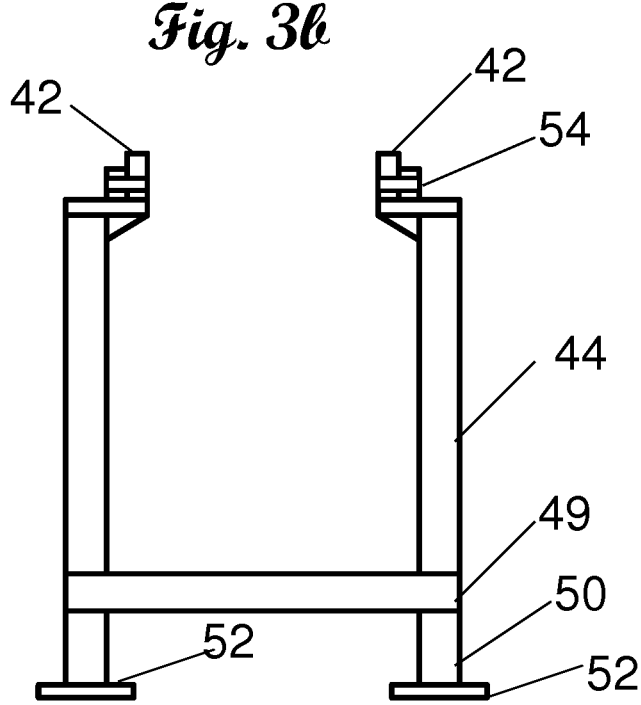
FIG. 3b is a front view of one embodiment of the modular base of the invention.
Figure 3C:
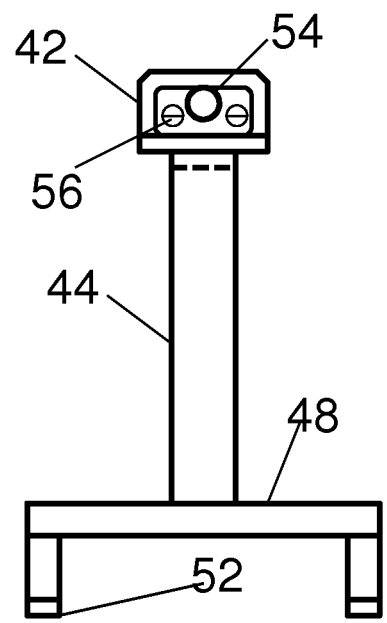
FIG. 3c is a side view of one embodiment of the modular base of the invention.

With reference to FIGS. 3*a*, 3*b* and 3*c*, a stationary horizontal base 40 comprising a pair of side members 48, a front and back member 49 disposed at right angles to the side members 48 forming a rectangular frame, a plurality of legs 50 extending below the frame and terminating in a foot 52, and a pair of upright members 44. Each of the upright members extend above the frame at a 90 degree angle relative to the frame and terminating in a bearing assembly 42 adapted to support the chamber and to receive the pair of pivot shafts 32 (See FIGS. 2*a* and 2*b*). The bearing assembly 42 includes a bearing surface 54 to permit the rotation of the chamber about the midpoint and a locking assembly 56 to lock the chamber in any position between vertical and horizontal with respect to the frame and the stationary horizontal base. The locking mechanism may be any device known to those skilled in the art for restraining the movement of the chamber with respect to the stationary horizontal base. Such locking mechanisms may include but are not limited to clamps, springs, thumb screws, levers and the like. The stationary horizontal base 40 can be constructed of materials selected from the group consisting of stainless steel, corrosion resistant alloy, metals having a fluoropolymer coating, and mixtures thereof.

Figure 4:
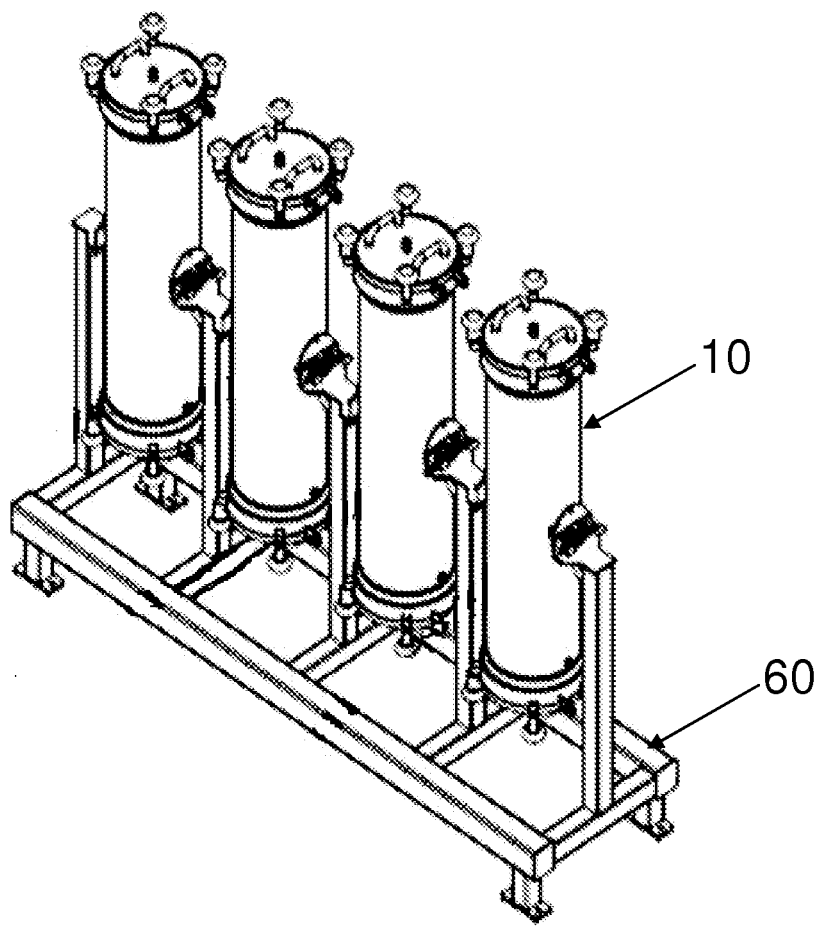
FIG. 4 is an isometric view of one embodiment of a multiple module apparatus of the invention.

Referring to FIG. 4, a multi-chamber installation is shown wherein 4 chambers 10 are supported as described hereinabove on a multi-chamber base 60. Each of the 4 chambers can be independently positioned between vertical and horizontal alignment for loading, unloading and maintenance from either the proximal or the distal end of the chamber. One embodiment of a multi-chamber apparatus for performing flash chromatography of the present invention comprises two or more of the modular apparatus disposed adjacent one to another. The multi-chamber apparatus can have any number of chambers supported by a multi-chamber base. Preferably, the multi-chamber apparatus for performing flash chromatography of the present invention comprises from 2, 3, 4, 5, 6, 7 or 8 chambers.

Figure 5:
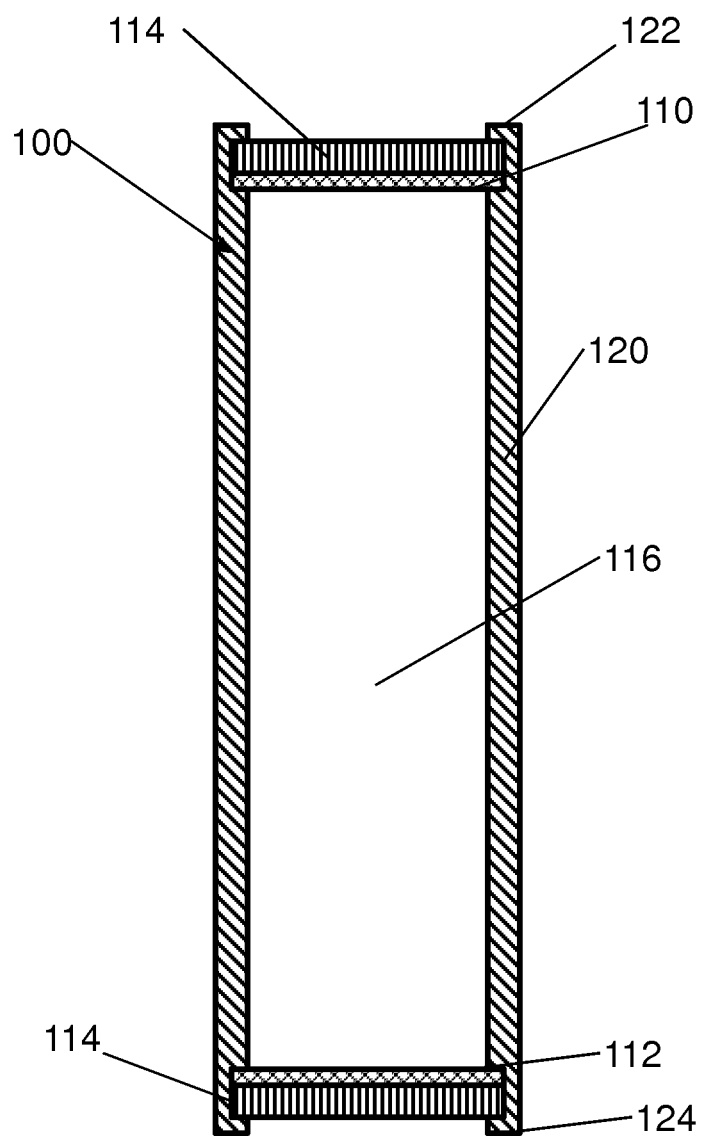
FIG. 5 is a cross-sectional view of one embodiment of a stationary phase adsorbent cartridge of the invention.

Referring to FIG. 5, a stationary phase adsorbent cartridge 100 is shown. The stationary phase adsorbent cartridge 100 is adapted to be removably disposed within the hollow cylindrical interior 2 of the chamber 10 (See FIG. 2*a*). The stationary phase adsorbent cartridge 100 has a cylindrical outer wall 120 and includes a first porous frit plate 110 sealingly disposed at the proximal end and a second porous frit plate 112 sealingly disposed at the distal end defining a hollow cartridge interior 116. A porous support plate 114 is disposed over the frit plate 110 on the distal end and at the proximal end to support the weight of the stationary phase adsorbent disposed in the hollow cartridge interior 116 and to provide structural stability to the stationary phase adsorbent cartridge 100. The frit plates 110 are made of high density polyethylene, HDPE, having a 35 micron pore size (depth filters) to prevent particles from entering the adsorbent cartridge. The porous support plate 114 is a perforated plate disposed at the proximal and distal ends of the cartridge to enhance the flow distribution through the cartridge. The porous support plate 114 can be made of high density polyethylene. A stationary phase adsorbent is disposed in the hollow cartridge interior 116. Additional spacers (not shown) may be disposed in the hollow cartridge when the stationary phase adsorbent does not completely fill the cartridge interior. A portion of the cylindrical outer wall 120 extends beyond the porous support plate forming a raised proximal ring 122 and a raised distal ring 124. The raised proximal ring and the raised distal ring optionally may chamfered where they contact the gasket. The raised proximal ring 122 is positioned within the sealing channel 35 of the proximal cover plate and the raised distal ring is positioned within the sealing channel of the distal cover plate when the cartridge is disposed in the chamber. When the stationary phase adsorbent cartridge 100 is disposed in the hollow cylindrical interior 2 of the chamber, the stationary phase adsorbent is in fluid communication with the hollow cylindrical interior 2 and the inlet and outlet nozzles 28 and 28'. The cylindrical outer wall 120 can be composed of polypropylene piping and is available in many different SDR Ratings. SDR 07 (230 psi) SDR 11 (150 psi/10.5 atmospheres), SDR 17 (88 psi/6.2 atmospheres), and SDR 33 (47 psi/3.3 atmospheres). A cylindrical outer wall comprising SDR 33 polypropylene pipe is preferred. The SDR or "Standard Dimension Ratio" is used by many pipe manufacturers as a method of rating pressure piping. SDR is a ratio of pipe diameter to wall thickness. The diameter of the cartridge may be of any size, but preferably between about 25 cm to 40 cm, more preferably between about 30 to 36 cm.

Figure 6:
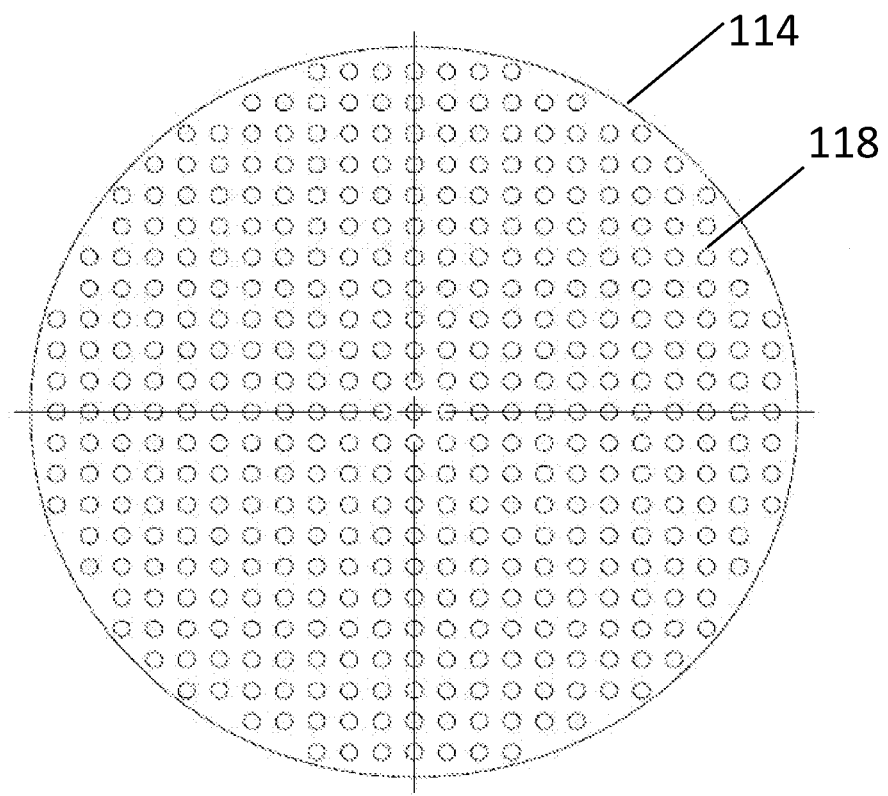
FIG. 6 is a top view of one embodiment of a support plate disposed in the stationary phase adsorbent cartridge of the invention.

With reference to FIG. 6, a top view of the porous support plate 114 (See FIG. 5). The porous support plate 114 has a plurality of perforations 118 extending through the porous support plate and distributed uniformly about the porous support plate.

In practice, a flash chromatography process, or flash chromatography, employs a compressible fluid as a mobile phase, to elute the sample containing a compound(s) of interest. More than one compressible fluid can be used, e.g., a mixture. Suitable compressible fluids include, for example, carbon dioxide, water, ammonia, nitrogen, nitrous oxide, methane, ethane, ethylene, propane, butane, n-pentane, benzene, methanol, ethanol, isopropanol, isobutanol, monofluoromethane, trifluoromethane, dimethyl sulfoxide, acetonitrile, hydrofluorocarbons, chlorotrifluoromethane, monofluoromethane, hexafluoroethane, 1,1-difluoroethylene, 1,2-difluoroethylene, toluene, pyridine, cyclohexane, m-cresol, decalin, cyclohexanol, O-xylene, tetralin, aniline, acetylene, chlorotrifluorosilane, xenon, sulfur hexafluoride, propane or a combination thereof.

A preferred compressible fluid is carbon dioxide, because it is nontoxic, inexpensive and widely available, as long as the sample requiring separation has some solubility in carbon dioxide.

The mobile phase may also contain a cosolvent, such as an organic solvent. A suitable solvent is chosen based on the polarity of the materials being separated and to increase the solubility of the sample in the compressible fluid. Preferably, the amount of cosolvent is less than 50 wt. %, based on the weight of the compressible fluid and cosolvent mixture combined, more preferably less than 40%, less than 30%, less than 20%, or even less than 10%. It is possible that no cosolvent will be required, although typically at least a small amount is necessary, e.g., about 1-10%, to improve solubility of the sample in the compressible fluid. One skilled in the art can easily select a suitable solvent based on the characteristics of the sample.

The mobile phase may be comprised of a single mobile phase, or more than one mobile phase, e.g., two or more mobile phases, such as three or four. The composition of the mobile phase or phases is determined by the required solvent strength of the mobile phase. Typically, the more polar the solvent mixture, the more polar the compounds that are separated, as would be understood by one skilled in the art. The compressible fluid and cosolvent can be delivered to the pressurized vessel in a mixed stream or in separate streams, according to the needs of the user.

The mobile phase is passed through a pressurized vessel containing an adsorption material, the vessel being pressurized to maintain the compressible fluid at the appropriate pressure. In one embodiment, the sample is first loaded into the pressurized vessel before the mobile phase is added, for example, if the sample is very viscous. In another embodiment, the sample can be premixed with the mobile phase, and the mixture is then loaded in the pressurized vessel. In yet another embodiment, the sample is dissolved in a solvent and introduced into the stream of the cosolvent prior to mixing the compressible fluid with the cosolvent. The solvent can be the same as or different from the cosolvent used in the mobile phase. In another embodiment the sample is injected into the mobile phase.

The present invention in various modes of operation results in rapid equilibration which means that there is very little time required between runs and the next injection can be almost immediately. Unfortunately, in normal phase HPLC, there is significant time spent equilibrating the column before the next run is started.

Suitable chromatography adsorption materials include silica-based materials, such as silica, silica gel or alumina of regular or irregular shape, and other column packing materials known to those skilled in the art of chromatography. A preferred packing material is silica.

Typical packing material in standard flash chromatography includes highly porous, irregular particles of sizes greater than 50 microns. Smaller particles can be used in the present invention than in traditional LC, HPLC or flash chromatography because there is a lower pressure drop from the top of the column to the bottom of the column, resulting from a less viscous mobile phase with higher diffusivities. Preferably, the particle size of the adsorption material used in the present invention ranges between about 10 to about 500 microns, more preferably, the particle size of the adsorption material used in the present invention ranges between about 10 to about 200 microns.

We claim:

1. A modular apparatus for performing flash chromatography comprising:
  a. a chamber having a cylindrical shell having a proximal end and a distal end, said cylindrical shell enclosing a hollow cylindrical interior, said cylindrical shell having an outer surface and an interior surface, a centerline and a midpoint along the centerline;
  b. a proximal annular ring and a distal annular ring, each annular ring being sealingly disposed at the proximal end and at the distal end of the cylindrical shell, respectively, each annular ring having an upper surface, a hinge and a plurality of mounting clamps distributed uniformly about each annular ring, said upper surface having a raised ring;
  c. a proximal cover plate and a distal cover plate, each cover plate having a center, an outer side, an underside, and a nozzle, the underside of each cover plate having disposed thereon a registration channel, a sealing channel concentric with the registration channel, and a plurality of radial flow distribution channels extending radially from a distribution hub at the center and extending toward the registration channel, said raised ring being adapted to be disposed in the registration channel when each cover plate is in a closed position on each annular ring, each cover plate being removably disposed on the annular ring at the distal end and at the proximal end of the cylindrical shell and rigidly attached to said hinge to register the cover plate on the annular ring and to permit the cover plate to be sealingly disposed on the annular ring and secured by said plurality of mounting clamps, said nozzle being in fluid communication with the hollow cylindrical interior;

d. a flash chromatographic cartridge disposed in the hollow cylindrical interior, said flash chromatographic cartridge comprising:
 i. a cylindrical cartridge shell having a proximal end and a distal end disposed in the hollow cylindrical interior, said cylindrical cartridge shell enclosing a hollow cartridge interior;
 ii. a first porous frit plate sealingly disposed at the proximal end and a second porous frit plate sealingly disposed at the distal end of the cylindrical cartridge shell;
 iii. a porous support plate disposed on the first and the second frit plate and rigidly attached to the cylindrical cartridge shell at the proximal end and at the distal end such that the cylindrical shell extends beyond the porous support plate to provide a raised proximal ring and a raised distal ring adapted to be positioned within the sealing channel of each cover plate adjacent to the cylindrical shell when each cover plate is in the closed position; and,
 iv. a stationary phase adsorbent disposed in the hollow cartridge interior wherein the stationary phase adsorbent is in fluid communication with the hollow cylindrical interior;

e. a gasket disposed in the sealing channel of each cover plate to provide a seal between each annular ring and each cover plate and between the cylindrical cartridge shell and each cover plate;

f. a pair of pivot shafts rigidly disposed on the outer surface of the cylindrical shell at the midpoint and extending outwardly from the outer surface along a line at right angles to the centerline;

g. a stationary horizontal base having a pair of upright members, each of the upright members extending above said base at a 90 degree angle relative to the stationary horizontal base and terminating in a bearing adapted to receive the pair of pivot shafts; wherein the cylindrical shell can be positioned vertically or horizontally relative to the stationary horizontal base and wherein the hinge is oriented in line with the pair of pivot shafts to permit said cover plates to be opened on a horizontal plane relative to the stationary horizontal base.

2. The apparatus of claim 1, further comprising disposing at least one handle on the outer side of the proximal and distal cover plates.

3. The apparatus of claim 1, wherein the cylindrical shell and the proximal and distal cover plates comprise material selected from the group consisting of stainless steel, corrosion resistant alloy, metals having a fluoropolymer coating, and mixtures thereof.

4. The apparatus of claim 1, wherein the cylindrical cartridge shell comprises polypropylene.

5. The apparatus of claim 1, wherein the first and second frit plates comprise high density polyethylene.

6. The apparatus of claim 1, wherein the first and second frit plates have a 35 micron pore size.

7. The apparatus of claim 1, further comprising a weep nozzle disposed on the cylindrical shell between the midpoint and the distal end, said weep nozzle being in fluid communication with the hollow cylindrical interior.

8. The apparatus of claim 1, wherein the gasket is in the form of an o-ring.

9. The apparatus of claim 1, wherein the gasket comprises a material selected from the group consisting of a fluoroelastomer resin, polytetrafluoroethylene, chlorinated polyethylene (CPE), and asbestos.

10. The apparatus of claim 1, wherein gasket comprises a silicon encapsulate with polytetrafluoroethylene.

11. A multi-chamber apparatus for performing flash chromatography comprising two or more of the modular apparatus of claim 1 disposed adjacent one to another.

12. The multi-chamber apparatus of claim 11, wherein the multi-chamber comprises from 2 to 8 chambers.

13. The apparatus of claim 1, further comprising disposing a pivot positioning wheel on at least one of the pivot shafts for manual movement of the chamber from a vertical position to a horizontal position.

14. The apparatus of claim 1, wherein said apparatus has an adsorbent capacity of from about 10 to about 50 kilograms of adsorbent.

15. The apparatus of claim 1, wherein said apparatus can be pressurized to operate over an operating pressure range of from about 100 psia (7.82 atm) to about 150 psia (11.23 atm).

16. The apparatus of claim 1, wherein said stationary phase adsorbent has a particle size of between about 10 to about 500 microns.

17. The apparatus of claim 1, further comprising disposing at least one spacer in the hollow cartridge interior when the stationary phase adsorbent does not completely fill the hollow cylindrical interior or to provide multiple chambers in the hollow cartridge interior.

18. A flash chromatography process comprising passing a sample containing a compound of interest and a compressible fluid over the stationary phase adsorbent disposed in the apparatus of claim 1.

* * * * *